US00PP14662P29

(12) United States Plant Patent
Zerr

(10) Patent No.: US PP14,662 P2
(45) Date of Patent: Mar. 30, 2004

(54) POINSETTIA PLANT NAMED 'FISOLYMP'

(50) Latin Name: *Euphorbia pulcherrima*
Varietal Denomination: Fisolymp

(75) Inventor: Katharina Zerr, Höhr-Grenzhausen (DE)

(73) Assignee: Florfis Ag (CH)

( * ) Notice: Subject to any disclaimer, the term of this patent is extended or adjusted under 35 U.S.C. 154(b) by 0 days.

(21) Appl. No.: 10/382,659

(22) Filed: Mar. 7, 2003

(51) Int. Cl.[7] ..... A01H 5/00
(52) U.S. Cl. ..... Plt./307
(58) Field of Search ..... Plt./307

*Primary Examiner*—Bruce R. Campell
*Assistant Examiner*—June Hwu
(74) *Attorney, Agent, or Firm*—Foley & Lardner

(57) ABSTRACT

The new Poinsettia 'Fisolymp' is described as having uniform, deep red bract color; medium sized inflorescence, ovate bracts and relatively many cyathia; uniform dark-green foliage, ovate leaves almost without lobes; medium sized, rounded plant habit; and early to medium flowering response.

1 Drawing Sheet

Latin name of the genus and species of the plant claimed: *Euphorbia pulcherrima.*
Variety denomination: Fisolymp.

BACKGROUND OF THE INVENTION

The present invention relates to a new and distinct cultivar of poinsettia plant known by the vareity denomination 'Fisolymp', and botanically known as *Euphorbia pulcherrima.*

'Fisolymp' was discovered by the inventor, Katharina Zerr, from an induced mutation in the variety 'Fismille' (U.S. Plant Pat. No. 13,660). 'Fismille' is characterized by large, bright red colored bracts, dark-green foliage almost without lobes, upright and moderately tall plant habit, and very early flowering time.

Irradiation of young plants of 'Fismille' was conducted in Ahrensburg, Germany, in May 1998. The treated plants were grown out in Hillscheid, Germany, and were propagated by cuttings. The flowering plants derived thereof were screened for positive mutations by Katharina Zerr, the inventor/breeder throughout 1999.

One plant, designated no. 373-1, was chos n b cause of its darker red bract color. Three months later the plant was multiplied by vegetative cuttings and the resulting plants were examined in the fall of 2000, and again in the fall of 2001. They proved to be uniform and stable.

Horticultural examination of the plants starting in 2001 and continuing thereafter has demonstrated that the combination of characteristics as herein disclosed for 'Fisolymp' are firmly fixed and retained through successive generations of asexual reproduction.

BRIEF SUMMARY OF THE INVENTION

The following traits have been repeatedly observed and are determined to be basic characteristics of 'Fisolymp', which in combination distinguish this Poinsettia as a new and distinct cultivar:

1. Uniform, deep red bract color;
2. Medium sized inflorescence, ovate bracts and relatively many cyathia;

3. Uniform dark-green foliage, ovate leaves almost without lobes;
4. Medium sized, rounded plant habit; and
5. Early to medium flowering response.

'Fisolymp' has not been observed under all possible environmental conditions. The phenotype may vary significantly with variations in environment such as temperature, light intensity, and day-length. The following observations, measurements and comparisons describe plants grown in Hillscheid, Germany, under greenhouse conditions which approximate those generally used in commercial practice.

Of the many commercial cultivars known to the inventor, the most similar in comparison to 'Fisolymp' is the parental cultivar 'Fismille'. In comparison to 'Fismille', 'Fisolymp' has smaller inflorescences with shorter bracts of somewhat deeper red bract color. Furthermore, plant habit is somewhat more rounded, slightly shorter and wider, less upright, and flowering response is not quite as early. The primary advantage of 'Fisolymp' is that it can be grown under the same culture regime as many other varieties, while the variety 'Fismille' is flowers earlier and may require extra treatment with growth regulator in order to avoid very large, overhanging bracts.

BRIEF DESCRIPTION OF THE DRAWINGS

The accompanying color photographic drawing shows typical inflorescence and foliage of 'Fisolymp', with colors being as true as possible with illustrations of this type. The photograph shows a mature potted plant.

DETAILED BOTANICAL DESCRIPTION

The plants described were grown in a greenhouse in Hillscheid, Germany, in the fall of 2002. Rooted cuttings were planted into 14 cm pots on Jul. 25, 2002 and were pinched on August 8, leaving 7–8 leaves. Initially, the temperature was between a minimum of 19° C. and 24.5° C. maximum (ventilation temperature), and lower beginning October 1, minimum 16° C. to 23° C. The plants initiated flowers und r short-day conditions under natural short-day conditions in fall, no black cloth was applied.

Observations and measurements were mainly taken in mid December, when the plants were in full flower and about 20 weeks old. In the following description color references are made to The Royal Horticultural Society Colour Chart (R.H.S.). The color values were determined indoors in a north light.

Plant:

*Form.*—Shrub, self-branching.

*Growth habit.*—About medium sized, pinched plants are bushy and round in shape.

*Height (above soil line).*—24.5 cm.

*Width.*—43.1 cm.

*Average number of branches.*—7.2.

*Length of branches.*—19–23 cm.

*Diameter of branches.*—6 mm.

*Average number of inflorescence.*—6.8.

*Stem color.*—Lower part light green, RHS 143 A to 143 B, upper parts of stems are partly reddish infused, the resulting color is approximately RHS 181 B. Internode length: 15–20 mm.

*Rooting.*—Medium, sufficiently rooted for transplanting after about 20–24 days in a greenhouse at a temperature of 22–24° C.

*Blooming habit.*—Begin under natural short day conditions in fall:botanically (cyathia open): around December 1, commercially (bracts colored, marketable): in late November.

*Flowering response time.*—About 8–9 weeks.

Foliage:

*Shape.*—Ovate, most often with truncate base, without or with very weak lobes and acute to acuminate tip, entire margins.

*Texture.*—Upper surface: Smooth and flat, only weakly veined, color of veins: Mainly light green, RHS 139 D, at the base pink, from RHS 182 A to RHS 182 B.

*Lower surface.*—Flat and smooth, except for the slightly protruding midrib and finer side veins in a pinnate pattern, the vein color is light pink, approximately RHS 182 B, near the base.

*Leaf blade size.*—Length: 11.5 cm; width 7.8 cm.

*Petiole.*—Length: 5.5 cm on average, diameter 0.3 cm.

*Quantity.*—About 35–40 leaves per plant. Color: Generally dark green, uniform.

*Mature foliage.*—Upper surface, RHS 139 A; under surface, RHS 139 B.

*New foliage.*—Upper side: RHS 143 A; under side RHS 137 D.

*Leaf petiole.*—Upper side: Purple, RHS 53 A to 53 B; lower side: RHS 53 C to 53 D.

*Aspect.*—Petioles are horizontally directed, while the leaf blades slant downwards.

Disease/pest resistance/susceptibility: No special observations made.

Flowering description:

*Whole inflorescence with surrounding bracts.*—About medium sized, with the bracts horizontally or slightly upward directed, middle with relatively many cyathia, surrounded by bracts in a rosette-like, overlapping arrangement.

*Diameter.*—About 21–23 cm.

*Height of inflorescence.*—About 3 cm.

*Number of bracts per inflorescence.*—11–13 (with a size over 2 cm).

*Keeping quality.*—Good lasting quality will be maintained for about 4 weeks, no dropping of bracts.

Bracts:

*Shape.*—Ovate, with rounded to acute bases, very weak lobes, and acuminate tips; bract blade is almost flat, less distinctly folded along th midrib than 'Fismille'.

*Size of the largest fully colored bract.*—10.5 cm long, 6.5 cm wide.

*Texture.*—Moderately rugose or rippled.

*Vein color.*—Upper side corresponds closely to bract color; lower side dull pink, near RHS 51 B.

*Color.*—Generally deep red, uniform; upper surface RHS 46 B; lower surface RHS 45 B, uniform.

*Petiole.*—18–22 mm long, color: upper side between RHS 46 A and 46 B, lower side 51 A.

*Cyme.*—22–26 mm in diameter, 10–15 cyathia borne in a cluster.

*Cyathium.*—Ovate, about 5–6 mm in diameter, medium to light green colored, RHS 143 B, top dark red, between RHS 46 A and 46 B; total length (with peduncle and female flower): 23 mm.

*Peduncle.*—Light green, RHS 143 C, partly brown, RHS 181 A, about 4–5 mm long.

*Nectar cups.*—Usually one per cyathium, about 5–6 mm wide, golden yellow to orange colored, RHS 23 A to 25 A, near margin reddish infused: RHS 40 A; the honey cups appear to open relatively early, quite some time before dehiscence of the stamens.

Reproductive organs:

*Stam ns.*—Appear relatively late (in mid-December), few in number, 1–5 in a clust r, filaments 3–4 mm, red RHS 46B; moderate pollen, yellow, RHS 12 A.

*Pistil.*—Style and stigma dark red, RHS 46 A, stigma trifurcate, 6-lobed.

*Ovaries.*—Light to medium green, RHS 143 C, initially obovate, later triangular, diameter 3–4 mm, 5–6 mm long, 3 ovules.

*Fruit/seed set.*—No seed set observed.

I claim:

1. A new and distinct Poinsettia plant named 'Fisolymp' as described and illustrated herein.

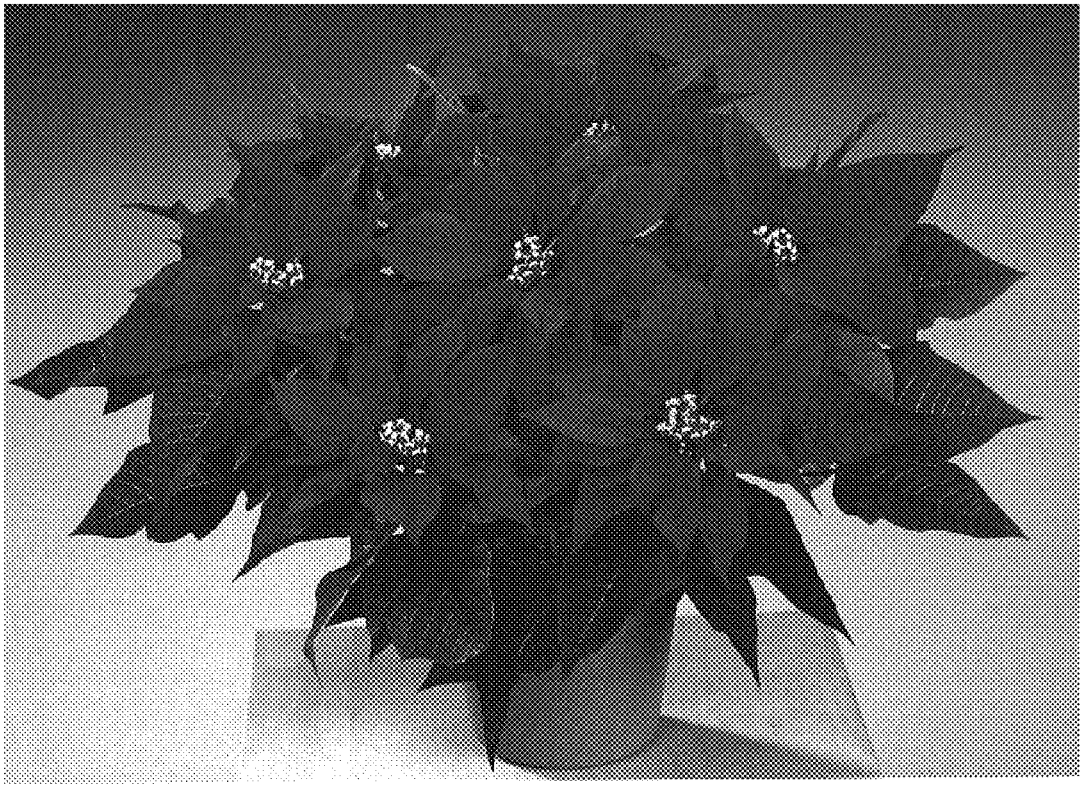

* * * * *